United States Patent [19]

Reifschneider

[11] 4,237,168

[45] Dec. 2, 1980

[54] N-(4-CHLORO-2-METHYLPHENYL)-N-HYDROXY METHANIMIDAMIDE AND ITS PESTICIDAL USE

[75] Inventor: Walter Reifschneider, Walnut Creek, Calif.

[73] Assignee: The Dow Chemical Company, Midland, Mich.

[21] Appl. No.: 47,512

[22] Filed: Jun. 11, 1979

[51] Int. Cl.$^3$ .................. A01N 37/52; C07C 131/00
[52] U.S. Cl. ............................. 424/326; 564/229
[58] Field of Search .................. 260/564 G; 424/327, 424/326

[56] References Cited

U.S. PATENT DOCUMENTS

| 3,434,526 | 12/1969 | Steinhausen et al. | 424/300 |
| 3,462,537 | 8/1969 | Merk | 424/326 |
| 3,502,720 | 3/1970 | Arndt | 260/564 RF |

FOREIGN PATENT DOCUMENTS 866194 4/1978 Belgium .
2717437 10/1978 Fed. Rep. of Germany .

OTHER PUBLICATIONS

Muller, G., "Berichte der Deutschen Chemischen Gesellschaft" (1889), pp. 2410–2411.

Primary Examiner—Natalie Trousof
Assistant Examiner—L. Hendriksen
Attorney, Agent, or Firm—S. Preston Jones; Ronald G. Brookens

[57] ABSTRACT

The compound N-(4-chloro-2-methylphenyl)-N'-hydroxy methanimidamide is prepared and used as an insecticide.

3 Claims, No Drawings

N-(4-CHLORO-2-METHYLPHENYL)-N-HYDROXY METHANIMIDAMIDE AND ITS PESTICIDAL USE

DESCRIPTION OF THE PRIOR ART

Various methanimidamides (formamidines) are taught in the prior art. For example, U.S. Pat. Nos. 3,462,537, 3,484,526 and 3,502,720 teach N-(substituted and unsubstituted phenyl)N',N'-dimethyl (or N'-methyl) formamidines and their use as insecticides. In addition, Belgium Pat. No. 866,194 (German Patent Application No. 2,717,437) discloses the instant N-(4-chloro-2-methylphenyl)-N'-hydroxy methanimidamide and its use as an insecticide.

SUMMARY OF THE INVENTION

The present invention is directed to the N-(4-chloro-2-methylphenyl)-N'-hydroxy methanimidamide which corresponds to the formula

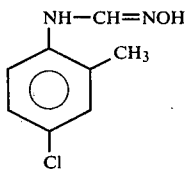

and its use as an insecticide for the control of various insects.

The compound of the present invention can be prepared by a variety of methods. For example, it can be prepared by the reaction of one molecular equivalent of N,N-dimethyl-N'-(4-chloro-2-methylphenyl)methanimidamide with from 1 to 10 molecular equivalents of one of hydroxylamine:hydrochloride.

The reaction can be characterized as follows:

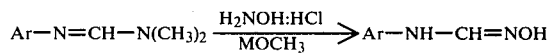

wherein M is sodium, potassium, lithium or cesium. (no attempt has been made to present a balanced equation)

In carrying out this reaction, N,N-dimethyl-N'-(4-chloro-2-methylphenyl)methanimidamide is mixed with the hydroxylamine:hydrochloride in the presence of an alkali metal methoxide solution containing excess methanol. The mixture is stirred at room temperature for from about 3 to about 20 hours. The reaction product is recovered by filtration and the filtrate is concentrated under reduced pressure to recover any additional product contained therein. The residue from the concentration step and the filter cake are combined and suspended in water, collected by filtration, water washed and the product recovered after being further purified by recrystallization from ethanol or aqueous ethanol.

Alternatively, the compound can be prepared by reacting one molecular equivalent of N-(4-chloro-2-methylphenyl)methanimidic acid; ethyl ester with an excess of hydroxylamine:hydrochloride and an alkali metal hydroxide in the presence of methanol as the reaction medium. The mixture is reacted, with agitation, at room temperature and the reaction is usually complete in from about 3 to about 20 hours. The solid product which forms is collected by filtration and usually additional product can be obtained by concentration of the filtrate under reduced pressure and the addition of the residue to the filter cake. The combined solids are triturated with water, collected by filtration, washed with water and the recovered product further purified by recrystallization from ethanol or aqueous ethanol.

This reaction can be characterized as follows:

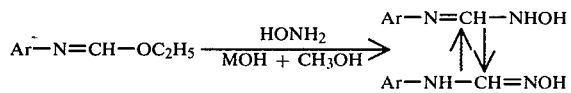

DESCRIPTION OF SOME PREFERRED EMBODIMENTS

Example I—N-(4-Chloro-2-methylphenyl)-N'-hydroxymethanimidamide

To a sodium methoxide solution prepared by dissolving 19 grams of sodium metal in 250 milliliters of methanol was added 56 grams of hydroxylamine:hydrochloride in 300 milliliters of methanol. To the resulting mixture was added 98 grams (0.5 mole) of N,N-dimethyl-N'-(4-chloro-2-methylphenyl)methanimidamide. The mixture was stirred at room temperature for 18 hours. The solid reaction product was recovered by filtration and the filtrate concentrated by evaporation under reduced pressure. The residue and the solid reaction product (filter cake) were suspended in water, collected by filtration, water washed and recrystallized from ethanol. The N-(4-chloro-2-methylphenyl)-N'-hydroxymethanimidamide product was recovered in a yield of 81.7 grams (89% of theoretical) and melted at 171°–171.5° C.

The new compound of the present invention possess excellent insecticidal and acaracidal properties and is very suitable in the control of chewing and sucking insects for the protection of plants and stored goods. The compound penetrates into the tissues of plants and is highly effective as a contact and stomach poison insecticide. Due to its low toxicity to warm-blooded animals, it is also suitable for the control of ecto- and endo-parasites on and in animals.

The compound of the present invention can be employed during any stage of the insect development, i.e. adult, larvae or egg.

In its use as an insecticide, an insecticidal amount of the compound per se or a composition incorporating an insecticidal amount of the compound is used as the toxicant for contact with the pest insect or its habitat. The insecticidal amount, of course, is that quantity which elicits toxic mortality among the treated pests. Generally, such insecticidal response results by contacting the target pests or their habitat with a composition containing from 0.00001 to 99 or more percent of the active compound in the total composition. Good results are achieved upon contact with a composition containing about 1000 parts of the active compound per million by weight.

Suitable compositions include those which are in the form of liquid solutions, liquid emulsifiable concentrates, and dust or granular preparations. Such can be further diluted as and where appropriate with conventional diluents.

Liquid compositions containing the active compound are prepared by dissolving the active compound in a suitable inert organic solvent such as acetone, toluene, xylene, methylene chloride, chlorobenzene, ethyl ether or petroleum distillates or by dispersing the active compound in water with or without the aid of a suitable surface acting dispersing agent such as can be provided by ionic or nonionic dispersing and emulsifying agents.

The aqueous compositions may contain one or more water-immiscible solvents for the toxicants. In such compositions, the carrier comprises an aqueous emulsion, that is, a mixture of water-immiscible solvent, emulsifying agent and water. The choice of dispersing and emulsifying agents and the amounts thereof employed is dictated by the nature of the composition type and by the ability of the agent to facilitate the dispersion of the active toxicant compound in the aqueous carrier to produce the desired composition. Dispersing and emulsifying agents which may be employed in the compositions include the condensation products of alkylene oxides with phenols and organic acids, alkylarylsulfonates, polyoxyethylene derivatives or sorbitan esters, complex ether alcohols, mahogany soaps, and the like. In such compositions, the surface active agents are usually employed in the amount of from 1 to 20 percent by weight of the combined weight of the surface active agent and the active compound.

In the preparation of dust compositions, the active compound is dispersed in and on a finely divided inert sold such as talcum, chalk, gypsum, and the like. In such operations, the carriers are mechanically ground with the compounds or wet with a volatile organic solvent solution thereof. Similarly dust compositions containing the compound may be prepared from bentonite, fuller's earth, attapulgite, and other clays. Depending upon the proportions of ingredients, these dust compositions may be employed as concentrates and subsequently diluted with additional solid surface acting dispersing agent or with talc, chalk, or gypsum and the like to obtain a desired amount of active agent in a composition adapted to be applied for insect control. Also, such concentrate dust compositions may be dispersed in water with or without the aid of a dispersing agent to form spray mixtures.

Granular formulations are conveniently prepared by impregnation, such as through simple mechanical mixing of the active compound in a presized carrier, usually of the type herebefore set forth.

In practice, the active compound is distributed so as to provide contact of the target insect with toxic amounts of the active compound. Such contact can be achieved through direct contact of the active compound with the target insect or by more indirect means such as by application to its food and/or habitat. Thus, for example, the active compound or a composition thereof can be spread throughout the environs of the target host so as to both provide direct and indirect contact thereof or bait compositions incorporating a toxic amount of the active compound or composition thereof can be readily prepared and strategically located so as to provide ultimate contact of the host species therewith.

The following examples serve to further typify the nature of the present invention and are given solely for the purpose of illustration.

Example II

25 Parts by weight of N-(4-chloro-2-methylphenyl)-N'-hydroxymethanimidamide, 60 parts of fuller's earth, 10 parts of diatomaceous earth, 3 parts of an alkyl aryl sulfonate (Naccanol NR) and 2 parts of a polymerized sodium salt of a substituted benzoid alkyl sulfonic acid (Daxad No. 27) are mechanically mixed and ground together to prepare a concentrate composition in the form of a wettable powder.

Similarly, 25 parts by weight of N-(4-chloro-2-methylphenyl)-N'-hydroxymethanimidamide, 65 parts xylene and 10 parts of a dimeric alkylated aryl polyether alcohol (Triton X-155), are mechanically mixed together to prepare a liquid emulsifiable concentrate composition.

In a like manner, 6 parts by weight of the N-(4-chloro-2-methylphenyl)-N'-hydroxy methanimidamide, 2 parts of Naccanol NR, 2 parts of Daxad No. 27, and 200 parts of water are ballmilled together to prepare a concentrate composition in the form of a water-dispersible liquid.

Example III

1 Part of N-(4-chloro-2-methylphenyl)-N'-hydroxy methanimidamide is mixed with 99 parts of purified kerosene to obtain an oil preparation having an active ingredient concentration of 1 percent. In application, the composition can be atomized or sprayed as is.

The concentrate compositions may be further diluted in their concentrate state and/or dispersed in water to prepare aqueous compositions which have desirable wetting and penetrating properties. These compositions are adapted to be employed to treat target insects and distribute the active compound in insecticidal concentrations.

Example IV

In this operation, an aqueous dispersion was prepared by admixing a predetermined amount of N-(4-chloro-2-methylphenyl)-N'-hydroxy methanimidamide dissolved in a suitable inert solvent, with a predetermined quantity of water and a predetermined amount of a surfactant to give aqueous dispersions containing varying predetermined amounts of the compound as the sole active toxicant. Separate 3 inch discs cut from tobacco plant leaves were thoroughly wetted by briefly dipping into one of the dispersions and the wetted leaves placed in an open Petri dish and permitted to dry. After the leaves were dry, 5 live tobacco budworm larvae, approximately late 2nd instar, were placed in each Petri dish. In identical operations, 5 like live tobacco budworm larvae were placed in control Petri dishes, the leaf therein having been wetted with a solution containing only water and surfactant. The dishes were maintained under moist conditions at about 80° F., conducive for the growth of the tobacco budworm larvae, for a period of about 2 days. At the end of the 2-day period, the dishes were examined to determine the minimum concentration in parts of the active compound per million parts of the ultimate dispersion necessary to give at least a 95 percent kill and control of the tobacco budworm larvae. The results of this examination are set forth below in Table I.

TABLE I

| Active Compound | Minimum Concentration in PPM of active compound in dispersion to give $LC_{95}$ for tobacco budworm larvae |
|---|---|
| N-(4-chloro-2-methylphenyl)-N'-hydroxy methanimidamide | 100 |
| Control | No Control |

Example V

Aqueous dispersions were prepared by admixing a predetermined amount of N-(4-chloro-2-methylphenyl)-N'-hydroxy methanimidamide dissolved in a suitable inert solvent, with a predetermined quantity of water and a predetermined amount of a surfactant to give aqueous dispersions containing varying predetermined amounts of the compound as the sole toxicant. Tobacco budworm adults were placed on separate tobacco seedlings and left on for one day. This permitted the budworms to lay eggs. One group of the seedlings was sprayed with one of the dispersions to run off. In like manner another group of the seedlings was sprayed to run off with a solution containing only water and surfactant. The seedlings were maintained under conditions conducive to the growth of the seedlings and tobacco budworm. After a period of two days, the seedlings were examined to determine the minimum concentration in parts of the active compound per million parts of the ultimate dispersions necessary to cause a failure to hatch of at least 90 percent of the tobacco budworm eggs. The results of this examination are set forth below in Table II.

TABLE II

| Active Compound | Minimum Concentration in PPM of active compound in dispersion to give $LC_{90}$ for tobacco budworm eggs |
| --- | --- |
| N-(4-chloro-2-methylphenyl)-N'-hydroxy methanimidamide | 22 |
| Control | No Control |

Example VI

Aqueous dispersions were prepared by admixing a predetermined amount of N-(4-chloro-2-methylphenyl)-N'-hydroxy methanimidamide dissolved in a suitable inert solvent, with a predetermined quanity of water and a predetermined amount of a surfactant to give aqueous dispersions containing varying predetermined amounts of the compound as the sole toxicant. Separate cotton plants were infested with approximately 100 two-spotted spider mites and the plants dipped into one of the dispersions. In a like manner, approximately 100 two-spotted spider mites were placed on control plants and the plants sprayed to run off with a solution containing only water and surfactant. The plants were maintained under conditions conducive to the growth of the plants and mites. After a period of five days, the plants were examined to determine the minimum concentration in parts of the active compound per million parts of the ultimate dispersion necessary to give at least 95 percent kill and control of the two-spotted spider mites. The results of this examination are set forth below in Table III.

TABLE III

| Active Compound | Minimum Concentration in PPM of active compound in dispersion to give $LC_{95}$ for two-spotted spider mites |
| --- | --- |
| N-(4-chloro-2-methylphenyl)-N'-hydroxy methanimidamide | 400 |
| Control | No Control |

In another operation, the compound of the present invention was found to give 100 percent kill and control of American dog tick when applied thereto in an aqueous dispersion containing the compound as the sole toxicant, at 250 parts of the compound per million parts of the ultimate dispersion.

In another operation, the above compound was found to give at least 50 percent kill and control of the cabbage looper when applied to the habitat thereof in an aqueous dispersion, as the sole toxicant, at 400 parts of the compound per million parts of the ultimate dispersion. In another operation, the above compound was found to give 100 percent kill and control of hornflies when applied thereto in an aqueous dispersion containing the compound, as the sole toxicant, at 1 part of the compound per million parts of the ultimate dispersion.

In another representative operation, the compound of the present invention was found to give at least 50 percent kill and control of codling moth when applied to either the eggs or larvae of the insect in an aqueous dispersion, as the sole toxicant, at 100 parts of the compound per million parts of the ultimate dispersion.

What is claimed is:

1. N-(4-chloro-2-methylphenyl)-N'-hydroxy methanimidamide.

2. An insecticidal composition comprising as the active ingredient, an insecticidally effective amount of N-(4-chloro-2-methylphenyl)-N'-hydroxy methanimidamide, in intimate admixture with an inert carrier therefor.

3. A method for the kill and control of insects which comprises contacting said insects or their habitat with a composition containing as the active ingredient, an insecticidally effective amount of N-(4-chloro-2-methylphenyl)-N'-hydroxy methanimidamide, in intimate admixture with an inert carrier therefor.

* * * * *